(12) United States Patent
Ujimoto et al.

(10) Patent No.: US 11,771,630 B2
(45) Date of Patent: Oct. 3, 2023

(54) OIL-BASED COSMETIC

(71) Applicant: Shiseido Company, Ltd., Tokyo (JP)

(72) Inventors: Kei Ujimoto, Tokyo (JP); Kouichi Nagai, Tokyo (JP); Marianne Ayaka Touati, Tokyo (JP); Yuko Nagare, Tokyo (JP); Satoshi Yamaki, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 184 days.

(21) Appl. No.: 17/267,330

(22) PCT Filed: Aug. 9, 2019

(86) PCT No.: PCT/JP2019/031596
§ 371 (c)(1),
(2) Date: Feb. 9, 2021

(87) PCT Pub. No.: WO2020/032242
PCT Pub. Date: Feb. 13, 2020

(65) Prior Publication Data
US 2021/0338552 A1 Nov. 4, 2021

(30) Foreign Application Priority Data

Aug. 10, 2018 (JP) .................. 2018-151678
May 15, 2019 (JP) .................. 2019-091903

(51) Int. Cl.
| | |
|---|---|
| *A61Q 17/04* | (2006.01) |
| *A61K 8/35* | (2006.01) |
| *A61K 8/04* | (2006.01) |
| *A61K 8/86* | (2006.01) |
| *A61Q 1/02* | (2006.01) |
| *A61Q 1/06* | (2006.01) |

(52) U.S. Cl.
CPC ............ *A61K 8/35* (2013.01); *A61K 8/042* (2013.01); *A61K 8/046* (2013.01); *A61K 8/86* (2013.01); *A61Q 17/04* (2013.01); *A61K 2800/262* (2013.01); *A61K 2800/43* (2013.01); *A61K 2800/48* (2013.01); *A61Q 1/02* (2013.01); *A61Q 1/06* (2013.01)

(58) Field of Classification Search
None
See application file for complete search history.

(56) References Cited

U.S. PATENT DOCUMENTS

| | | |
|---|---|---|
| 2003/0103930 A1 | 6/2003 | Uchida et al. |
| 2007/0178053 A1 | 8/2007 | Franklin et al. |
| 2010/0158824 A1* | 6/2010 | Lin .............. A61Q 19/00 524/588 |
| 2010/0209365 A1 | 8/2010 | Takakura et al. |
| 2012/0093747 A1 | 4/2012 | Kamimoto et al. |
| 2012/0142788 A1 | 6/2012 | Koehler et al. |
| 2018/0271757 A1* | 9/2018 | Nagai ................ A61Q 17/04 |
| 2018/0289610 A1* | 10/2018 | Yamaki ............... A61K 8/39 |
| 2020/0375874 A1* | 12/2020 | Naoi .................. A61K 8/73 |
| 2021/0338544 A1 | 11/2021 | Nagare et al. |
| 2021/0338545 A1 | 11/2021 | Ujimoto et al. |

FOREIGN PATENT DOCUMENTS

| | | |
|---|---|---|
| EP | 1 920 762 A1 | 5/2008 |
| EP | 1 996 155 A1 | 12/2008 |
| EP | 2 156 819 A1 | 2/2010 |
| EP | 3 213 741 A1 | 9/2017 |
| EP | 3 213 742 A1 | 9/2017 |
| EP | 3 357 484 A1 | 8/2018 |
| JP | 2006-052155 A | 2/2006 |
| JP | 2009-024012 A | 2/2009 |
| JP | 2009-132638 A | 6/2009 |
| JP | 2010-275206 A | 12/2010 |
| JP | 2012-012351 A | 1/2012 |
| JP | 2016-094361 A | 5/2016 |
| JP | 2017-149699 A | 8/2017 |
| JP | 2018-062504 A | 4/2018 |
| WO | WO-2005/070372 A1 | 8/2005 |
| WO | WO-2011/027710 A1 | 3/2011 |
| WO | WO-2016/068300 A1 | 5/2016 |

(Continued)

OTHER PUBLICATIONS

Database GNPD [Online] Mintel, "Anti-Imperfections, Mattifying Skin-Renewing Sun Care SPF 30," Vichy, Jul. 27, 2018, Database Accession No. 5855409, XP055599233, 4 pages.

(Continued)

*Primary Examiner* — Brian Gulledge
(74) *Attorney, Agent, or Firm* — Foley & Lardner LLP

(57) ABSTRACT

The present invention relates to an oil-based cosmetic having the innovative, unprecedented property in which the ultraviolet protection effects increase due to heat. The oil-based cosmetic of the present invention contains (A) an ultraviolet protectant; and
(B) at least one compound that is water-soluble and that has an IOB of 5.0 or lower, selected from among (i) alkylene oxide derivatives and (ii) polyhydric alcohols; wherein the (B) (i) alkylene oxide derivatives are polyoxyalkylene/polyoxyethylene copolymer dialkyl ethers represented by the following formula (I):

$$R_1O\text{-}[(AO)_m(EO)_n]\text{-}R_2 \quad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, $1 \leq m \leq 70$, $1 \leq n \leq 70$ and $m+n \leq 40$; and the oil-based cosmetic has a water content of 5% by mass or less.

10 Claims, No Drawings

(56) References Cited

FOREIGN PATENT DOCUMENTS

WO  WO-2017/057676 A1      4/2017
WO  WO-2018198800 A1 *  11/2018  ........... A61K 8/0229

OTHER PUBLICATIONS

Database GNPD [Online] Mintel, "Clear Stick UV Protector Wetforce Broad Spectrum 50+," Shiseido, Apr. 16, 2018, Database accession No. 5535307, XP055905017, 6 pages.

Database GNPD [Online] Mintel, "Intensive Spots Serum," Albion, May 31, 2017, Database accession No. 4848273, XP055903908, 5 pages.

Database GNPD [Online] Mintel, "Protection Lotion SPF 30," Shiseido, Jul. 13, 2015, Database Accession No. 3336055, XP055641565, 6 pages.

Database GNPD [Online] Mintel, "UV Lip Color Splash SPF 30," Shiseido, May 2, 2018, Database accession No. 5650271, XP055905023, 5 pages.

Shiseido International, Japan, Perfect UV Protector SFP 50+/PA++++ for Sensitive Skin & Children, Mintel GPND, Jun. 2016, retrieved Oct. 15, 2019, ID#4057965, from URL: https://portal.mintel.com.

Whitening Essence Facial UV Sunscreen SPF 50+/PA++++, ID#4100943, Mintel GNPD, online, Jun. 2016, retrieved on Oct. 11, 2019, from URL: https://portal.mintel.com.

Kose, Pure Bright Foundation, Mintel GNPD, online, Apr. 2003, retrieved on Oct. 25, 2019, ID#200747, from URL: https://portal.mintel.com.

Shiseido, Pressed Powder SPF15/PA++, Mintel GNPD, online, Feb. 2015 (retrieved on Oct. 25, 2019, ID#2952765, from URL: https://portal.mintel.com.

Shiseido, Sun Protection Lip Treatment, Mintel GNPD, online, Oct. 2005, retrieved on Oct. 25, 2019, ID#406984, from URL: https://portal.mintel.com.

Shiseido, UV Protective Lip Treatment 30, Mintel GNPD, online, Aug. 2017, retrieved on Oct. 25, 2019, ID#5005209, from URL: https://portal.mintel.com.

* cited by examiner

OIL-BASED COSMETIC

CROSS-REFERENCE TO RELATED APPLICATIONS

This application is the U.S. National Stage of PCT/JP2019/031596, filed Aug. 9, 2019, which claims priority to JP 2018-151678, filed Aug. 10, 2018 and JP 2019-091903, filed May 15, 2019.

TECHNICAL FIELD

The present invention relates to an oil-based cosmetic having sunscreen effects. More specifically, the present invention relates to an oil-based cosmetic having the unprecedented property in which heating increases the ultraviolet protection effects over those immediately after applying the cosmetic.

BACKGROUND ART

Cosmetics having sunscreen effects have the effects of reducing the amount of ultraviolet rays reaching the skin on which the cosmetics have been applied and thereby suppressing the harmful impact thereof on the skin due to the action of ultraviolet absorbing agents or ultraviolet scattering agents blended into the cosmetics.

As an indicator of the ultraviolet protection effects of cosmetics, Sun Protection Factor (SPF) is the most widely known, representing the ultraviolet protection effects as an SPF value (for example, "SPF 30", etc.). In Japan, PFA (Protection Factor of UVA) or UVAPF (UVA Protection Factor of product) is used for ultraviolet rays in the UVA range, and the degree of UVA protection effects of a product is represented by PA (Protection grade of UVA) class ("PA++", etc.), which is based on the PFA or the UVAPF. In the United States, Critical Wavelength (CW), which indicates the balance of UVA and UVB protection effects, is used.

In recent years, in order to suppress the harmful impact of ultraviolet rays on the skin, cosmetics that provide high ultraviolet protection effects across a wide wavelength range from the UVA to the UVB ranges have come to be sought. For example, sunscreen products boasting SPF factors of 50 or higher (50+) and PA++++ have come onto the market.

The ultraviolet protection effects due to sunscreen products are obtained by the ultraviolet protectants, i.e., by the ultraviolet absorbing agents or ultraviolet scattering agents that are blended therein. However, ultraviolet absorbing agents include some in which the ultraviolet absorption performance decreases due to irradiation by light (photodegradation). Additionally, ultraviolet absorbing agents and ultraviolet scattering agents can flow away from the skin surface upon coming into contact with moisture.

Many improvements have been proposed for suppressing the photodegradation of ultraviolet protection effects (Patent Document 1), and regarding water resistance, a cosmetic having the innovative property in which contact with moisture does not decrease the ultraviolet protection effects but conversely increases the protection effects has been developed (Patent Document 2).

Meanwhile, as with light and moisture, decreases in ultraviolet protection effects due to heat cannot be ignored. In general, when heat is applied to a cosmetic that has been applied to skin, the ultraviolet absorbing agents and other components contained in the cosmetic are degraded, thereby decreasing the ultraviolet protection effects. However, regarding heat, although there are examples in which the impact of heat, for example, on the emulsion stability of emulsion cosmetics including cosmetics have been considered (Patent Document 3), changes in the ultraviolet protection effects due to heat have not been considered until now, and cosmetics having the purpose of suppressing decreases in ultraviolet protection effects due to heat have not previously been proposed.

RELATED ART

Patent Documents

Patent Document 1: WO 2017/057676
Patent Document 2: WO 2016/068300
Patent Document 3: JP 4397286 B

SUMMARY OF THE INVENTION

Problem to be Solved by the Invention

The present invention is based on the discovery, in a research process for developing a cosmetic having ultraviolet protection effects, that ultraviolet protection effects do not decrease, but conversely increase, due to heat applied in the usage environment, and an objective is to provide an oil-based cosmetic having the innovative, unprecedented property in which the ultraviolet protection effects increase due to heat.

Means for Solving the Problem

As a result of performing diligent research towards solving the above-mentioned problem, the present inventors discovered that an oil-based cosmetic having the novel properties that are the above-mentioned objective can be obtained by blending an ultraviolet protectant with a specific alkylene oxide derivative or polyhydric alcohol, and restricting the amount of moisture to be within a prescribed range, thereby completing the present invention.

In other words, the present invention provides an oil-based cosmetic containing
(A) an ultraviolet protectant; and
(B) at least one compound that is water-soluble and that has an IOB of 5.0 or lower, selected from among (i) alkylene oxide derivatives and (ii) polyhydric alcohols;
wherein
the (B) (i) alkylene oxide derivatives are polyoxyalkylene/polyoxyethylene copolymer dialkyl ethers represented by the following formula (I):

$$R_1O\text{-}[(AO)_m(EO)_n]\text{-}R_2 \qquad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, $1 \leq m \leq 70$, $1 \leq n \leq 70$ and $m+n \leq 40$; and
the oil-based cosmetic has a water content of 5% by mass or less.

Effects of the Invention

With the oil-based cosmetic of the present invention, due to the above-mentioned features, rather than the ultraviolet protection effects being degraded when exposed to heat during actual use, the ultraviolet protection effects can be significantly increased over those immediately after the cosmetic has been applied to the skin. In other words, the oil-based cosmetic according to the present invention is an innovative cosmetic having the property, contrary to conventional expectations, in which heat, which had been considered to cause degradation of the effects in conventional cosmetics, conversely increase the ultraviolet protection effects.

MODES FOR CARRYING OUT THE INVENTION

The oil-based cosmetic of the present invention is characterized by containing (A) an ultraviolet protectant and (B) a prescribed alkylene oxide derivative or polyhydric alcohol, and in that the water content is 5% by mass or less. Hereinafter, the components constituting the oil-based cosmetic of the present invention will be described in detail.

<(A) Ultraviolet Protectant (Ultraviolet Absorbing Agent and/or Ultraviolet Scattering Agent)>

The (A) ultraviolet protectant (hereinafter sometimes referred to simply as "component (A)") blended into the oil-based cosmetic of the present invention refers to an ultraviolet absorbing agent and/or an ultraviolet scattering agent, and a type that is normally blended into cosmetics may be used.

The ultraviolet absorbing agents that can be used in the present invention are not particularly limited, and examples include benzoic acid derivatives, salicylic acid derivatives, cinnamic acid derivatives, dibenzoyl methane derivatives, β,β-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g. "Escalol 507"; ISP), glyceryl PABA, PEG-25-PABA (e.g. "Uvinul P25"; BASF), diethylamino hydroxybenzoyl hexyl benzoate (e.g. "Uvinul A Plus") and the like.

Examples of salicylic acid derivatives include homosalate ("Eusolex HMS"; Rona/EM Industries), ethylhexyl salicylate or octyl salicylate (e.g. "Neo Heliopan OS"; Haarmann & Reimer), dipropylene glycol salicylate (e.g. "Dipsal"; Scher), TEA salicylate (e.g. "Neo Heliopan TS"; Haarmann & Reimer) and the like.

Examples of cinnamic acid derivatives include octyl methoxycinnamate or ethylhexyl methoxycinnamate (e.g. "Parsol MCX"; DSM), isopropyl methoxycinnamate, isoamyl methoxycinnamate (e.g. "Neo Heliopan E1000"; Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g. "Parsol 1789"; DSM) and the like.

Examples of β,β-diphenyl acrylate derivatives include octocrylene (e.g. "Uvinul N539T"; BASF) and the like.

Examples of benzophenone derivatives include benzophenone-1 (e.g. "Uvinul 400"; BASF), benzophenone-2 (e.g. "Uvinul D50"; BASF), benzophenone-3 or oxybenzone (e.g. "Uvinul M40"; BASF), benzophenone-4 (e.g. "Uvinul MS40"; BASF), benzophenone-5, benzophenone-6 (e.g. "Helisorb 11"; Norquay), benzophenone-8 (e.g. "Spectra-Sorb UV-24"; American Cyanamid), benzophenone-9 (e.g. "Uvinul DS-49"; BASF), benzophenone-12 and the like.

Examples of benzylidene camphor derivatives include 3-benzylidene camphor (e.g. "Mexoryl SD"; Chimex), 4-methylbenzylidene camphor, benzylidene camphor sulfonic acid (e.g., "Mexoryl SL"; Chimex), camphor benzalkonium methosulfate (e.g. "Mexoryl SO"; Chimex), terephthalylidene dicamphor sulfonic acid (e.g. "Mexoryl SX"; Chimex), polyacrylamide methylbenzylidene camphor (e.g. "Mexoryl SW"; Chimex) and the like.

Examples of phenylbenzimidazole derivatives include phenylbenzimidazole sulfonic acid (e.g. "Eusolex 232"; Merck), disodium phenyldibenzimidazole tetrasulfonate (e.g. "Neo Heliopan AP"; Haarmann & Reimer) and the like.

Examples of triazine derivatives include bis-ethylhexyloxyphenol methoxyphenyl triazine (e.g. "Tinosorb S"; Ciba Specialty Chemicals), ethylhexyl triazone (e.g. "Uvinul T150"; BASF), diethylhexyl butamido triazone (e.g. "Uvasorb HEB"; Sigma 3V), 2,4,6-tris(diisobutyl-4'-aminobenzalmalonate)-s-triazine, 2,4,6-tris[4-(2-ethylhexyloxycarbonyl)anilino]-1,3,5-triazine and the like.

Examples of phenylbenzotriazole derivatives include drometrizole trisiloxane (e.g. "Silatrizole"; Rhodia Chimie), methylene bis(benzotriazolyl tetramethylbutyl phenol) (e.g. "Tinosorb M" (Ciba Specialty Chemicals)) and the like.

Examples of anthranil derivatives include menthyl anthranilate (e.g. "Neo Heliopan MA"; Haarmann & Reimer) and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups (e.g. Polysilicone-15; "Parsol SLX"; DSM Nutrition Japan) and the like.

Examples of 4,4-diarylbutadiene derivatives include 1,1-dicarboxy (2,2'-dimethylpropyl)-4,4-diphenylbutadiene and the like.

Examples of particularly preferred ultraviolet absorbing agents include, but are not limited to, ethylhexyl methoxycinnamate, octocrylene, dimethicodiethyl benzalmalonate, polysilicone-15, 4-tert-butyl-4'-methoxy dibenzoyl methane (t-butyl methoxy dibenzoyl methane), ethylhexyl triazone, diethylamino hydroxybenzoyl hexyl benzoate, bis-ethylhexyloxyphenol methoxyphenyl triazine, oxybenzone-3, methylene bis-benzotriazolyl tetramethylbutyl phenol, phenylbenzimidazole sulfonic acid, 3-(4'-methylbenzylidene)-d,l-camphor, 3-benzylidene-d,l-camphor, homosalate and ethylhexyl salicylate. Of the above, good ultraviolet protection increase effects can be obtained when at least octocrylene is contained as component (A).

However, when 4-tert-butyl-4'-methoxy dibenzoyl methane is blended, the blended amount thereof should preferably be 10% by mass or less relative to the total amount of component (A). This is because 4-tert-butyl-4'-methoxy dibenzoyl methane has a tendency to hinder the increase in ultraviolet protection effects due to heating when the (B) alkylene oxide derivative or polyhydric alcohol is added, thus making it difficult to actually experience an enhancement of the ultraviolet protection effects due to heat.

The ultraviolet scattering agent used in the present invention is not particularly limited, but specific examples include fine-particle metal oxides such as, for example, zinc oxide, titanium oxide, iron oxide, cerium oxide and tungsten oxide.

The ultraviolet scattering agent may be non-surface-treated or may be treated with various types of hydrophobic surface treatments, but those that are hydrophobically surface-treated are preferably used. As the surface treatment agent, it is possible to use a type that is commonly used in the cosmetics field including, for example, a silicone such as dimethicone and alkyl-modified silicone, an alkoxysilane such as octyltriethoxysilane, a dextrin fatty acid ester such as dextrin palmitate, or a fatty acid such as stearic acid.

The (A) ultraviolet protectant in the present invention includes embodiments consisting only of an ultraviolet absorbing agent, embodiments consisting only of an ultraviolet scattering agent, and embodiments including both an ultraviolet absorbing agent and an ultraviolet scattering agent.

Although the blended amount of the (A) ultraviolet protectant is not particularly limited, the amount should normally be at least 5% by mass, for example, 5% to 40% by mass, preferably 6% to 40% by mass, and more preferably 7% to 35% by mass relative to the total amount of the oil-based cosmetic. If the blended amount of the (A) ultraviolet protectant is less than 5% by mass, then sufficient ultraviolet protection effects are difficult to obtain, and even if more than 40% by mass is blended, an increase in the ultraviolet protection effects commensurate with the blended amount cannot be expected, and the stability is worsened.

<(B) Alkylene Oxide Derivative or Polyhydric Alcohol>

The (B) (i) alkylene oxide derivative or (ii) polyhydric alcohol (hereinafter sometimes referred to simply as "component (B)") blended into the cosmetic of the present invention is often blended as a humectant in normal cosmetics. In the present invention, by blending a specific alkylene oxide derivative or polyhydric alcohol, the ultraviolet protection effects after being heated can be significantly increased in comparison to those immediately after the cosmetic has been applied to the skin.

The (B) (i) alkylene oxide derivative or the (ii) polyhydric alcohol must be water-soluble. If a type that is not water-soluble is used, then the ultraviolet protection increase effects will tend to be lowered by heating. In the present invention, "water-soluble" means that at least 0.1% by mass dissolves in water at 25° C.

Additionally, the (B) (i) alkylene oxide derivative or the (ii) polyhydric alcohol has an IOB of 5.0 or lower, more preferably 3.0 or lower, and even more preferably 2.5 or lower. If the IOB value is too high, then there are cases in which ultraviolet protection performance increase effects due to heat cannot be sufficiently obtained. On the other hand, the lower limit of the IOB value is not particularly limited, but should preferably be at least 0.5, and more preferably at least 0.8.

In this case, IOB is an abbreviation for Inorganic/Organic Balance, which is a value representing the ratio of the inorganic value to the organic value, and which serves as an indicator of the degree of polarity of an organic compound. The IOB value is specifically represented by IOB value=inorganic value/organic value. Regarding the "inorganic value" and the "organic value" respectively, an "inorganic value" and an "organic value" are set for various types of atoms or functional groups so that, for example, the "organic value" is 20 for one carbon atom in a molecule and the "inorganic value" is 100 for one hydroxyl group. The IOB value of an organic compound can be computed by summing the "inorganic values" and the "organic values" of all of the atoms and functional groups in that organic compound (see, for example, Yoshio Koda, "*Yuki Gainenzu—Kiso to Oyo—*" [Organic Conceptual Diagram—Fundamentals and Applications], pp. 11-17, Sankyo Shuppan, 1984).

Furthermore, the (B) (i) alkylene oxide derivative or (ii) polyhydric alcohol preferably has an ether bond. By having an ether bond, the component can be expected to more easily dissolve in water than a component not having an ether bond, while also being able to dissolve in oil.

Examples of the (i) alkylene oxide derivative that may be used in the present invention include the polyoxyalkylene/polyoxyethylene copolymer dialkyl ethers represented by the following formula (I):

$$R_1O\text{-}[(AO)_m(EO)_n]\text{-}R_2 \quad (I)$$

In the above formula, AO denotes an oxyalkylene group having 3 to 4 carbon atoms. Specific examples include an oxypropylene group, an oxybutylene group, an oxyisobutylene group, an oxytrimethylene group and an oxytetramethylene group, among which an oxypropylene group and an oxybutylene group are preferred. EO represents an oxyethylene group.

$R_1$ and $R_2$, each independently, represent a hydrogen atom or a hydrocarbon group having one to four carbon atoms. Examples of hydrocarbon groups include methyl groups, ethyl groups, n-propyl groups, isopropyl groups, n-butyl groups, sec-butyl groups and tert-butyl groups. Methyl groups and ethyl groups are preferred.

The $R_1$ and $R_2$ in each molecule may be the same type of hydrocarbon group, a mixture of a hydrocarbon group and a hydrogen atom, or a mixture of multiple hydrocarbon groups having different numbers of carbon atoms. However, for each of $R_1$ and $R_2$, the ratio between the numbers of hydrocarbon groups and hydrogen atoms that are present should be such that the ratio (Y/X) of the number (Y) of hydrogen atoms to the number (X) of hydrocarbon groups is preferably 0.15 or lower, and more preferably 0.06 or lower.

The symbol m represents the average number of moles of AO added, such that $1 \leq m \leq 70$, preferably $2 \leq m \leq 20$, and more preferably $2 \leq m \leq 10$. The symbol n represents the average number of moles of EO added, such that $1 \leq n \leq 70$, preferably $2 \leq n \leq 20$, and more preferably $2 \leq n \leq 10$. Additionally, m+n is 40 or less, preferably 25 or less, and more preferably 20 or less. In particular, if m+n is 20 or less, then significantly superior ultraviolet protection increase effects due to heating can be obtained.

The order of addition of AO and EO is not particularly limited. AO and EO may be added in the form of blocks so as to form a block copolymer, or may be randomly added so as to form a random copolymer. Block copolymers include not only copolymers with two blocks, but also those with three or more blocks. Preferably, a random copolymer is used.

The molecular weight of the polyoxyalkylene/polyoxyethylene copolymer dialkyl ether represented by formula (I) should be 100 to 10000, preferably 150 to 5000, more preferably 200 to 3000, and even more preferably 300 to 2000. The ratio [EO/(AO+EO)] of the amount of EO to the total amount of AO and EO in each molecule is preferably 20% to 80% by mass.

Specific examples of polyoxyalkylene/polyoxyethylene copolymer dialkyl ethers that can be favorably used in the present invention include, but are not limited to, the following polyoxypropylene/polyoxyethylene copolymer dimethyl ethers:

PEG/PPG-9/2 dimethyl ether
PEG/PPG-17/4 dimethyl ether
PEG/PPG-14/7 dimethyl ether
PEG/PPG-11/9 dimethyl ether
PEG/PPG-55/28 dimethyl ether
PEG/PPG-36/41 dimethyl ether PEG/PPG-6/3 dimethyl ether
PEG/PPG-8/4 dimethyl ether
PEG/PPG-6/11 dimethyl ether
PEG/PPG-14/27 dimethyl ether The polyoxyalkylene/polyoxyethylene copolymer dialkyl ether tends to have better ultraviolet protection performance increase effects due to heat as the molecular weight becomes relatively smaller. Therefore, among the polyoxypropylene/polyoxyethylene copolymer dimethyl ethers listed above, PEG/PPG-9/2 dimethyl ether exhibits the strongest effects.

Meanwhile, examples of the (ii) polyhydric alcohol that can be used in the present invention include the polyalkylene glycols of formula (II) below, as well as butylene glycol, dipropylene glycol, diglycerin, propanediol, erythritol, xylitol, methylglyceth-10, sorbitol and the like.

In this case, the polyalkylene glycols are represented by the following formula (II):

$$\text{HO(RO)}_p\text{H} \tag{II}$$

In the above formula, RO denotes an oxyalkylene group having two to four carbon atoms, and p is 3 to 500.

Specifically, it is selected from among those that are used in cosmetics, and includes polyethylene glycol (also represented by "PEG"), polypropylene glycol (also represented by "PPG") and polybutylene glycol (also represented by "PBG") and the like.

Among the above, polyethylene glycols in which, in formula (II) above, RO is an oxyethylene group, and p is in the range 3 to 500, more preferably 3 to 60, are preferred. The preferred average molecular weight of the polyethylene glycol is within the range 150 to 23000, more preferably 150 to 3000. Specific examples include polyethylene glycol 300, polyethylene glycol 400, polyethylene glycol 1500, polyethylene glycol 20000 and the like.

The polyalkylene glycol tends to have better ultraviolet protection performance increase effects due to heat as the molecular weight becomes relatively smaller. Therefore, among the polyethylene glycols listed above, particularly strong effects are obtained when polyethylene glycol 300 or polyethylene glycol 400 is used.

Component (B) in the present invention includes embodiments consisting only of an alkylene oxide derivative, embodiments consisting only of a polyhydric alcohol, and embodiments including both an alkylene oxide derivative and a polyhydric alcohol.

In particular, in order to maximum the ultraviolet protection performance increase effects due to heat, at least one each of an alkylene oxide derivative and a polyhydric alcohol are preferably included. For example, in the case in which a combination of a low-molecular-weight polyoxypropylene/polyoxyethylene copolymer dimethyl ether having an average molecular weight of 150 to 3000 is combined with a polyalkylene glycol having an average molecular weight of 150 to 3000, the ultraviolet protection performance increase effects due to heat become prominent. Specific examples include, in particular, a combination of polyethylene glycol 300 and PEG/PPG-9/2 dimethyl ether, and a combination of polyethylene glycol 400 and PEG/PPG-9/2 dimethyl ether.

The blended amount of component (B) should be at least 1.0% by mass or more, more preferably 2.5% by mass or more, and 30% by mass or less, more preferably 25% by mass or less relative to the total amount of the oil-based cosmetic. If the blended amount is less than 1.0% by mass, then there are cases in which ultraviolet protection performance increase effects due to heat cannot be sufficiently obtained. In particular, if the amount is 2.5% by mass or more, then the effects can be more reliably achieved. Additionally, if the amount exceeds 30% by mass, then the stability and the usability may be affected.

<Water>

The oil-based cosmetic of the present invention, like conventional oil-based cosmetics, contains substantially no water, but may contain water within a range not compromising the effects, the appearance, the usability and the like of the present invention. However, when containing water, the amount thereof must be suppressed so as to be 5% by mass or less, more preferably 3% by mass or less relative to the total amount of the oil-based cosmetic. If the water content is too high, then there are cases in which the stability of the oil-based cosmetic is lost and the cosmetic becomes cloudy.

<Optional Blended Components>

Aside from the above-mentioned component (A) and component (B), components that are normally used in cosmetics may be blended into the oil-based cosmetic of the present invention within a range not compromising the effects of the present invention. For example, it is possible to appropriately blend solidifiers, oils, lower alcohols, powder components and the like.

Solidifiers are components for gelling or thickening oils, including, for example, dextrin fatty acid esters such as dextrin palmitate and dextrin myristate; sucrose fatty acid esters such as sucrose caprylic acid esters; solid or semi-solid hydrocarbon oils such as vaseline, hydrogenated palm oil and hydrogenated castor oil; organically modified clay minerals such as distearyldimonium hectorite and benzyldimethylstearyl ammonium hectorite; higher fatty acids that have 8 to 22 carbon atoms and that are solid at ambient temperature, such as lauric acid, myristic acid, palmitic acid, stearic acid, 12-hydroxystearic acid and the like, or salts thereof; and amino acid-based gelling agents such as dibutyllauroyl glutamide, dibutylethyl hexanoyl glutamide, polyamide-8 and polyamide-3.

Additionally, the oils that can be blended into the oil-based cosmetic of the present invention may be polar or non-polar, and a wide variety of oils that are commonly used in cosmetics may be used. Examples include ester oils such as diisopropyl sebacate, isopropyl myristate, diethylhexyl succinate, glyceryl tri-2-ethylhexanoate, pentaerythrityl tetra-2-ethylhexanoate, cetyl 2-ethylhexanoate, alkyl benzoates having twelve to fifteen carbon atoms and isononyl isononanoate; hydrocarbon oils such as liquid paraffin, squalane, isododecane, isohexadecane and hydrogenated polyisobutene; silicone oils such as dimethicone, hexamethyl cyclotrisiloxane, octamethyl tetracyclosiloxane, decamethyl cyclopentasiloxane, dodecamethyl cyclohexasiloxane and diphenylsiloxyphenyl trimethicone; and liquid oils and fats such as palm oil, linseed oil, camellia oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cottonseed oil, soybean oil, peanut oil, tea seed oil, evening primrose oil, egg yolk oil, liver oil, triglycerin, glyceryl trioctanoate, glyceryl triisopalmitate and isostearic acid.

Examples of lower alcohols include alcohols having one to five carbon atoms, such as ethanol and isopropanol.

Additionally, a spherical powder is preferably further contained. By blending in a spherical powder, stickiness is suppressed, the texture is improved, and a good, silky touch can be obtained. The spherical resin powder may be arbitrarily used without any particular restrictions, as long as it is of a type that is blended into cosmetic products or the like in general. Examples include (meth)acrylic acid ester resin powders, polyamide resin powders (nylon powders), polyethylene powders, polystyrene powders, copolymer resin powders of styrene and (meth)acrylic acid, benzoguanamine resin powders, polytetrafluoroethylene powders, cellulose powders, trimethyl silsesquioxane powders and the like, as well as organopolysiloxane elastomer spherical powders or composite spherical powders having the above as base powders. The average particle size of the spherical powder is preferably 3 to 20 µm. If the size is smaller than 3 µm, then an effect of suppressing stickiness cannot be observed, and if the size is larger than 20 µm, then graininess conversely occurs. The blended amount of the spherical powder is not particularly limited, but is preferably 3% to 30% by mass, more preferably 7% to 20% by mass.

An example of a commercially available spherical organic resin powder is Ganzpearl (AICA Kogyo), and examples of commercially available spherical silicone resin powders include Trefil E-505C, Trefil E-506C, Trefil E-506S, Trefil HP40T (all Toray Dow Corning Silicone), Tospearl 2000B (Momentive Performance Materials), silicone powders KSP-100 and KSP-300 (Shin-Etsu Chemical), and the like.

Additionally, aside from the above, components that are normally used in cosmetics may be blended into the oil-based cosmetic of the present invention within a range not compromising the effects of the present invention, in accordance with the format being prepared. For example, it is possible to appropriately blend, as needed, pH adjusters, chelating agents, preservatives, antioxidants, medicinal agents, alcohols, colorants, pigments and the like. Examples of medicinal agents include ascorbic acid (vitamin C), tranexamic acid, kojic acid, ellagic acid, albutin, alkoxysalicylic acid, nicotinic acid amide, glycyrrhizinic acid, tocopherol, retinol, and salts or derivatives of the above (e.g., sodium L-ascorbate, L-ascorbic acid ester magnesium salts, L-ascorbic acid glucoside, 2-O-ethyl-L-ascorbic acid, 3-O-ethyl-L-ascorbic acid, 4-methoxysalicylic acid sodium salts, 4-methoxysalicylic acid potassium salts, dipotassium glycyrrhizinate, stearyl glycyrrhizinate, tocopherol acetate, retinol acetate, retinol palmitate, etc.).

The present invention may be provided in the form of a general oil-based cosmetic. Specific formats include liquids, gels, solids and the like, which may be manufactured by using conventional methods appropriate for each format.

When in gel form, the viscosity of the oil-based cosmetic at 25° C. should preferably be 300 mPa·s or higher, and more preferably 500 mPa·s or higher. If the viscosity is 300 mPa·s or higher, then sufficiently high ultraviolet protection effects can be achieved. In the present specification, the viscosity refers to the maximum viscosity measured with a Brookfield viscometer (spindle no. 7, rotation speed 5 rpm).

When in solid form, the hardness of the oil-based cosmetic at 25° C. should preferably be 5 N or higher, and more preferably 30 N or higher. If the hardness is 5 N or higher, then high ultraviolet protection effects can be obtained. Although the upper limit of the hardness is not particularly limited, it should preferably be 300 N or lower in consideration of the usability. The hardness in the present invention refers to a value measured with a Rheotech rheometer (pressure-sensitive shaft 5φ, needle penetration speed 2 cm/min, needle penetration depth 3 mm).

The oil-based cosmetic of the present invention may be prepared in an unseparated single-phase form. The oil-based cosmetic is preferably an unseparated single phase because, in that case, the cosmetic can be applied without being mixed by being shaken immediately before use. In the present invention, "unseparated single phase" refers to a state in which the liquid components contained in the cosmetic are mutually compatible and form a single phase. This state can be confirmed by visual observation.

Additionally, the oil-based cosmetic of the present invention can be prepared in a transparent state. In the present invention, "transparent" refers to a state wherein, when a cell with an optical path length of 10 mm is filled and the transmittance of light at a wavelength of 700 nm is measured with a spectrophotometer, the transmittance is at least 50% or higher.

The oil-based cosmetic of the present invention may be provided not only as a sunscreen cosmetic, but also as a makeup base or a makeup cosmetic such as a foundation provided with sunscreen effects, a hair cosmetic (including various types of hair-care products such as hairsprays and hair treatments for protecting the hair or scalp from ultraviolet rays), a spray-type cosmetic or the like.

The oil-based cosmetic of the present invention has the novel property in which the ultraviolet protection effects of a coating film are increased by heat. In this case, "the ultraviolet protection effects are increased by heat" refers to the case in which the thermal reaction rate, as determined by the following expression, from an absorbance integral value of a pre-heat treatment coating film (unheated sample) from 280 to 400 nm measured with a spectrophotometer or the like and an absorbance integral value of a post-heat treatment coating film (heated sample) that has been similarly measured, exceeds 100%.

Thermal reaction rate (%)=(post-heat treatment absorbance integral value)/(pre-heat treatment absorbance integral value)×100

In the oil-based cosmetic of the present invention, the thermal reaction rate exceeds at least 100%, preferably at least 103%, more preferably at least 105%, even more preferably at least 110%, and particularly preferably at least 115%.

When investigating the increase in the ultraviolet protection effects due to heat, the heating temperature should preferably be within the range from 30° C. to 70° C. For example, the temperature may be 32° C. or higher, 35° C. or higher, 37° C. or higher, or 40° C. or higher, and 65° C. or lower, 60° C. or lower, 55° C. or lower, or 50° C. or lower. If the heating temperature exceeds 70° C., then there may be problems such as a resin-composed measurement plate melting or the like.

In order to accurately evaluate the impact of heat, the heating time should preferably be 1 minute or longer, more preferably 10 minutes or longer. The upper limit of the heating time is not particularly limited, but should normally be 60 minutes or shorter, preferably 30 minutes or shorter.

EXAMPLES

Hereinafter, the present invention will be explained in further detail by providing specific examples. However, the present invention is not limited to the examples below. Additionally, the blended amounts in the following examples and the like are indicated in percentage by mass where not particularly indicated otherwise. Before specifically explaining each example, the evaluation method that was used will be explained.

(1) Post-Thermal Irradiation Absorbance Integral Value Change (Thermal Reaction Rate)

Prepared oil-based cosmetics were dripped, in the amount of 2 mg/cm², onto skin-simulating PMMA plates (SPFMASTER-PA01), applied with a finger for 60 seconds, and dried for 15 minutes to form coating films. Using an uncoated plate as a control, the absorbances (280 to 400 nm) of the coating films were measured with a Hitachi U-3500 self-recording spectrophotometer, and the obtained measurement data was used to determine pre-heat treatment absorbance integral values.

Next, the plates having the coating films were placed in isothermic tanks for 30 minutes at 37° C., and the absorbance integral values were determined in a manner similar to the above.

The changes (thermal reaction rate) in the absorbance integral values from before to after thermal irradiation were computed from the following equation.

Thermal reaction rate (%)=(post-heat treatment absorbance integral value)/(pre-heat treatment absorbance integral value)×100

(2) Presence or Absence of Phase Separation

The appearances of the prepared oil-based cosmetics were visually observed to determine whether the liquid components form a single phase in a compatible state (unseparated single phase), or some of the liquid components are not compatible with other liquid components and separation occurs (phase separation).

(3) Transparency

Cells having an optical path length of 10 mm were filled with prepared oil-based cosmetics, and the transmittances of light having a wavelength of 700 nm were measured with a spectrophotometer (Hitachi U3510).

Those in which the transmittance was 50% or higher were evaluated as being "transparent".

(4) Viscosity

The viscosities of the prepared oil-based cosmetics were measured by using a Brookfield viscometer (spindle no. 7, rotation speed 5 rpm) at 25° C.

(5) Hardness

The hardnesses of the prepared oil-based cosmetics were measured with a Rheotech rheometer (pressure-sensitive shaft 5ϕ, needle penetration speed 2 cm/min, needle penetration depth 3 mm) at 25° C.

Test Examples 1 to 7

For each of the test examples indicated in Table 1 below, all of the components were mixed by using a homomixer to obtain a liquid sunscreen cosmetic.

TABLE 1

|  | Test Ex. 1 | Test Ex. 2 | Test Ex. 3 | Test Ex. 4 | Test Ex. 5 | Test Ex. 6 | Test Ex. 7 |
| --- | --- | --- | --- | --- | --- | --- | --- |
| Ethanol | bal | bal | bal | bal | bal | bal | bal |
| PEG/PPG-9/2 dimethyl ether (IOB = 1.5) | 20 | — | — | — | — | — | — |
| PEG/PPG-14/7 dimethyl ether (IOB = 1.3) | — | 20 | — | — | — | — | — |
| Polyethylene glycol 300 (IOB = 2.3) | — | — | 20 | — | — | — | — |
| Polyethylene glycol 1500 (IOB = 2) | — | — | — | 20 | — | — | — |
| Dipropylene glycol (IOB = 1.8) | — | — | — | — | 20 | — | — |
| Glycerin (IOB = 6) | — | — | — | — | — | 20 | — |
| Ethylhexyl methoxycinnamate | 5 | 5 | 5 | 5 | 5 | 5 | 5 |
| 4-tert-Butyl-4'-methoxybenzoyl methane | 3 | 3 | 3 | 3 | 3 | 3 | 3 |
| Octyl salicylate | 5 | 5 | 5 | 5 | 5 | 5 | 5 |
| bis-Ethylhexyloxyphenol methoxyphenyl triazine | 2 | 2 | 2 | 2 | 2 | 2 | 2 |
| Octocrylene | 5 | 5 | 5 | 5 | 5 | 5 | 5 |
| Diethylamino hydroxybenzoyl hexyl benzoate | 2 | 2 | 2 | 2 | 2 | 2 | 2 |
| Diisopropyl sebacate | 5 | 5 | 5 | 5 | 5 | 5 | 5 |
| Total | 100 | 100 | 100 | 100 | 100 | 100 | 100 |
| Thermal reaction rate | 145% | 109% | 132% | 123% | 142% | 83% | 100% |
| Phase separation | unseparated single phase | unseparated single phase | unseparated single phase | unseparated single phase | unseparated single phase | phase separation | unseparated single phase |

As shown in Table 1, by blending in an alkylene oxide derivative or a polyhydric alcohol that is water-soluble and that has an IOB of 5.0 or lower as component (B), an increase in the ultraviolet protection effects by heating was observed (Test examples 1 to 5). However, said effects could not be observed when glycerin (IOB value=6.0), which is a polyhydric alcohol but with an IOB that is too high, was used, and when component (B) was not blended (Test examples 6 and 7). Additionally, for both alkylene oxide derivatives and polyhydric alcohols, a tendency for the ultraviolet protection effects due to heat to largely increase for those having lower molecular weights was observed.

Test Examples 8 to 13

For each of the test examples indicated in Table 2 below, all of the components were mixed by using a homomixer to obtain a liquid sunscreen cosmetic.

TABLE 2

|  | Test Ex. 8 | Test Ex. 9 | Test Ex. 10 | Test Ex. 11 | Test Ex. 12 | Test Ex. 13 |
|---|---|---|---|---|---|---|
| Ethanol | bal | bal | bal | bal | bal | bal |
| PEG/PPG-9/2 dimethyl ether | 20 | 10 | 5 | 3 | 1 | — |
| Ethylhexyl methoxycinnamate | 5 | 5 | 5 | 5 | 5 | 5 |
| 4-tert-Butyl-4'-methoxybenzoyl methane | 3 | 3 | 3 | 3 | 3 | 3 |
| Octyl salicylate | 5 | 5 | 5 | 5 | 5 | 5 |
| bis-Ethylhexyloxyphenol methoxyphenyl triazine | 2 | 2 | 2 | 2 | 2 | 2 |
| Octocrylene | 5 | 5 | 5 | 5 | 5 | 5 |
| Diethylamino hydroxybenzoyl hexyl benzoate | 2 | 2 | 2 | 2 | 2 | 2 |
| Diisopropyl sebacate | 5 | 5 | 5 | 5 | 5 | 5 |
| Total | 100 | 100 | 100 | 100 | 100 | 100 |
| Thermal reaction rate | 145% | 139% | 123% | 107% | 101% | 100% |
| Phase separation | unseparated single phase | unseparated single phase | unseparated single phase | unseparated single phase | unseparated single phase | phase separation |

As shown in Table 2, an increase in the ultraviolet protection effects by heating was not observed when component (B) was not blended (Test example 13). On the other hand, said effects were able to be observed when component (B) was blended (Test examples 8 to 12). In particular, effects of a degree that was sufficient to be actually experienced were observed when the blended amount of component (B) was 2.5% by mass or more.

Test Examples 14 to 20

For each of the test examples indicated in Table 3 below, all of the components were mixed by using a homomixer to obtain an oil-based sunscreen cosmetic. In the cases in which a solidifier was included, the solidifier was added to the oil-based components, the mixture was heated and melted, and after a humectant was added, mixed and homogenized, and thereafter cooled to obtain a solid sunscreen cosmetic.

TABLE 3

|  | Test Ex. 14 | Test Ex. 15 | Test Ex. 16 | Test Ex. 17 | Test Ex. 18 | Test Ex. 19 | Test Ex. 20 |
|---|---|---|---|---|---|---|---|
| Diisopropyl sebacate | bal | bal | bal | bal | bal | bal | bal |
| Hydrogenated polydecene | 20 | 20 | 20 | 20 | 20 | 20 | 20 |
| Diphenylsiloxyphenyl trimethicone | 2 | 2 | 2 | 2 | 2 | 2 | 2 |
| PEG/PPG-9/2 dimethyl ether | — | — | 15 | 15 | 15 | 15 | 15 |
| Ethylhexyl methoxycinnamate | 10 | 10 | 10 | 10 | 10 | 10 | 10 |
| 4-tert-Butyl-4'-methoxybenzoyl methane | 3 | 3 | 3 | 3 | 3 | 3 | 3 |
| Homosalate | 10 | 10 | 10 | 10 | 10 | 10 | 10 |
| bis-Ethylhexyloxyphenol methoxyphenyl triazine | 2 | 2 | 2 | 2 | 2 | 2 | 2 |
| Octocrylene | 5 | 5 | 5 | 5 | 5 | 5 | 5 |

TABLE 3-continued

|  | Test Ex. 14 | Test Ex. 15 | Test Ex. 16 | Test Ex. 17 | Test Ex. 18 | Test Ex. 19 | Test Ex. 20 |
| --- | --- | --- | --- | --- | --- | --- | --- |
| Diethylamino hydroxybenzoyl hexyl benzoate | 3 | 3 | 3 | 3 | 3 | 3 | 3 |
| Hydroxystearic acid | — | 6 | — | 10 | — | — | 6 |
| Polyamide-8 | — | 2 | — | — | 10 | — | 2 |
| Dibutyllauroyl glutamide | — | 2 | — | — | — | 5 | 2 |
| Total | 100 | 100 | 100 | 100 | 100 | 100 | 100 |
| Thermal reaction rate | 97% | 98% | 120% | 104% | 117% | 110% | 103% |

As shown in Table 3, by blending component (B), an increase in the ultraviolet protection effects by heating was observed (Test examples 16 to 20). Additionally, these effects were obtained even with cosmetics in which a solidifier was blended so as to put the cosmetics in solid form (Test examples 17 to 20).

Test Examples 21 to 26

For each of the test examples indicated in Table 4 below, all of the components were mixed by using a homomixer to obtain an oil-based sunscreen cosmetic. In the cases in which a solidifier was included, the solidifier was added to the oil-based components, the mixture was heated and melted, and after a humectant was added, mixed and homogenized, and thereafter cooled to obtain a solid sunscreen cosmetic.

TABLE 4

|  | Test Ex. 21 | Test Ex. 22 | Test Ex. 23 | Test Ex. 24 | Test Ex. 25 | Test Ex. 26 |
| --- | --- | --- | --- | --- | --- | --- |
| Hydrogenated polydecene | bal | bal | bal | bal | bal | bal |
| Diisopropyl sebacate | 30 | 30 | 30 | 30 | 30 | 30 |
| PEG/PPG-9/2 dimethyl ether | 15 | 15 | 15 | 15 | 15 | 15 |
| 4-tert-Butyl-4'-methoxybenzoyl methane | 3 | 3 | 3 | 3 | 3 | 3 |
| Ethylhexyl methoxycinnamate | 10 | 10 | 10 | 10 | 10 | 10 |
| Octocrylene | 5 | 5 | 5 | 5 | 5 | 5 |
| Diethylamino hydroxybenzoyl hexyl benzoate | 3 | 3 | 3 | 3 | 3 | 3 |
| bis-Ethylhexyloxyphenol methoxyphenyl triazine | 2 | 2 | 2 | 2 | 2 | 2 |
| Homosalate | 10 | 10 | 10 | 10 | 10 | 10 |
| Dextrin palmitate | — | 1 | 3 | 5 | 10 | 15 |
| Total | 100 | 100 | 100 | 100 | 100 | 100 |
| Viscosity (mPa · s) | 80 | 110 | 320 | 570 | 8340 | 44200 |
| Post-thermal irradiation absorbance (300 nm) | 1.45 | 1.53 | 1.96 | 2.29 | 2.65 | 2.79 |
| Thermal reaction rate | 110% | 111% | 107% | 108% | 105% | 101% |

As shown in Table 4, when the viscosity of the oil-based cosmetic was high, there was a tendency for the margin of increase in the ultraviolet protection effects by heating to become smaller (Test examples 22 to 26). However, after thermal irradiation of the coating film, the value of the absorbance at 300 nm itself increased as the viscosity increased, as a result of which high sunscreen effects were obtained.

Test Examples 27 to 32

For each of the test examples indicated in Table 5 below, all of the components were mixed by using a homomixer to obtain an oil-based sunscreen cosmetic. In the cases in which a solidifier was included, the solidifier was added to the oil-based components, the mixture was heated and melted, and after a humectant was added, mixed and homogenized, and thereafter cooled to obtain a solid sunscreen cosmetic.

TABLE 5

|  | Test Ex. 27 | Test Ex. 28 | Test Ex. 29 | Test Ex. 30 | Test Ex. 31 | Test Ex. 32 |
| --- | --- | --- | --- | --- | --- | --- |
| Hydrogenated polydecene | bal | bal | bal | bal | bal | bal |
| Diisopropyl sebacate | 30 | 30 | 30 | 30 | 30 | 30 |
| PEG/PPG-9/2 dimethyl ether | 15 | 15 | 15 | 15 | 15 | 15 |
| 4-tert-Butyl-4'-methoxybenzoyl methane | 3 | 3 | 3 | 3 | 3 | 3 |
| Ethylhexyl methoxycinnamate | 10 | 10 | 10 | 10 | 10 | 10 |
| Octocrylene | 5 | 5 | 5 | 5 | 5 | 5 |
| Diethylamino hydroxybenzoyl hexyl benzoate | 3 | 3 | 3 | 3 | 3 | 3 |
| bis-Ethylhexyloxyphenol methoxyphenyl triazine | 2 | 2 | 2 | 2 | 2 | 2 |
| Homosalate | 10 | 10 | 10 | 10 | 10 | 10 |
| Dibutyllauroyl glutamide | — | 0.1 | 0.5 | 1 | 3 | 5 |
| Polyamide-8 | — | 0.2 | 1 | 2 | 6 | 10 |
| Total | 100 | 100 | 100 | 100 | 100 | 100 |
| Hardness | 0 | 0 | 7 | 15 | 148 | 207 |
| Post-thermal irradiation absorbance (300 nm) | 1.45 | 1.6 | 1.75 | 1.77 | 2.42 | 2.52 |
| Thermal reaction rate | 110% | 117% | 114% | 112% | 105% | 103% |

As shown in Table 5, when the hardness of the oil-based cosmetic was high, there was a tendency for the margin of increase in the ultraviolet protection effects by heating to become smaller (Test examples 28 to 32). However, after thermal irradiation of the coating film, the value of the absorbance at 300 nm itself increased as the hardness increased, as a result of which high sunscreen effects were obtained.

Test Examples 33 to 38

For each of the test examples indicated in Table 6 below, a solidifier was added to the oil-based components, the mixture was heated and melted, and after a humectant was added, mixed and homogenized, and thereafter cooled to obtain a gel-type sunscreen cosmetic.

As shown in Table 6, although an increase in the ultraviolet protection effects by heating was observed in all of the test examples, the transmittance decreased significantly and clouding was observed when the amount of moisture contained in the oil-based cosmetics increased (Test example 37 and 38).

Test Examples 39 to 42

For each of the test examples indicated in Table 7 below, all of the components were mixed by using a homomixer to obtain a liquid sunscreen cosmetic.

TABLE 6

|  | Test Ex. 33 | Test Ex. 34 | Test Ex. 35 | Test Ex. 36 | Test Ex. 37 | Test Ex. 38 |
| --- | --- | --- | --- | --- | --- | --- |
| Isododecane | bal | bal | bal | bal | bal | bal |
| Diisopropyl sebacate | 15 | 15 | 15 | 15 | 15 | 15 |
| Water | — | 1 | 4 | 5 | 6 | 7 |
| Ethanol | 40 | 40 | 40 | 40 | 40 | 40 |
| Vinyl pyrrolidone/N,N'-dimethylaminoethyl methacrylate/stearyl acrylate/tripropylene glycol diacrylate copolymer | 2 | 2 | 2 | 2 | 2 | 2 |
| Isostearic acid | 3 | 3 | 3 | 3 | 3 | 3 |
| PEG/PPG-9/2 dimethyl ether | 10 | 10 | 10 | 10 | 10 | 10 |
| t-Butyl methoxy dibenzoyl methane | 3 | 3 | 3 | 3 | 3 | 3 |
| Ethylhexyl methoxycinnamate | 10 | 10 | 10 | 10 | 10 | 10 |
| bis-Ethylhexyloxyphenol methoxyphenyl triazine | 1 | 1 | 1 | 1 | 1 | 1 |
| Diethylamino hydroxybenzoyl hexyl benzoate | 2 | 2 | 2 | 2 | 2 | 2 |
| Ethylhexyl triazone | 3 | 3 | 3 | 3 | 3 | 3 |
| Total | 100 | 100 | 100 | 100 | 100 | 100 |
| Thermal reaction rate | 108% | 109% | 109% | 110% | 106% | 114% |
| Transmittance (700 nm) | 100% | 100% | 86% | 66% | 17% | 9% |

TABLE 7

|  | Test Ex. 39 | Test Ex. 40 | Test Ex. 41 | Test Ex. 42 |
|---|---|---|---|---|
| Ethanol | bal | bal | bal | bal |
| PEG/PPG-9/2 dimethyl ether | 20 | 20 | 20 | 20 |
| Ethylhexyl methoxycinnamate | 8 | 8 | 8 | 8 |
| Octyl salicylate | 5 | 5 | 5 | 5 |
| bis-Ethylhexyloxyphenol methoxyphenyl triazine | 2 | 2 | 2 | 2 |
| Octocrylene | 5 | 5 | 5 | 5 |
| Diethylamino hydroxybenzoyl hexyl benzoate | 2 | 2 | 2 | 2 |
| Diisopropyl sebacate | 5 | — | — | — |
| Glyceryl tri-2-ethylhexanoate | — | 5 | — | — |
| Isopropyl myristate | — | — | 5 | — |
| Cetyl ethylhexanoate | — | — | — | 5 |
| Total | 100 | 100 | 100 | 100 |
| Thermal reaction rate | 140% | 136% | 137% | 134% |
| Phase separation | unseparated single phase | unseparated single phase | unseparated single phase | unseparated single phase |

As shown in Table 7, an increase in the ultraviolet protection effects by heating was observed even when changing the type of oil that was blended (Test examples 39 to 42).

Test Examples 43 to 50

For each of the test examples indicated in Table 8 below, all of the components were mixed by using a homomixer to obtain a liquid sunscreen cosmetic.

TABLE 8

|  | Test Ex. 43 | Test Ex. 44 | Test Ex. 45 | Test Ex. 46 | Test Ex. 47 | Test Ex. 48 | Test Ex. 49 | Test Ex. 50 |
|---|---|---|---|---|---|---|---|---|
| Ethanol | bal | bal | bal | bal | bal | bal | bal | bal |
| Diisopropyl sebacate | 30 | 30 | 30 | 30 | 30 | 30 | 30 | 30 |
| PEG/PPG-9/2 dimethyl ether | 15 | 15 | 15 | 15 | — | — | — | — |
| Polyethylene glycol 300 | — | — | — | — | 15 | 15 | 15 | 15 |
| 4-tert-Butyl-4'-methoxybenzoyl methane | 0.5 | 1 | 2 | 3 | 0.5 | 1 | 2 | 3 |
| Ethylhexyl methoxycinnamate | 9.5 | 9 | 8 | 7 | 9.5 | 9 | 8 | 7 |
| Octocrylene | 5 | 5 | 5 | 5 | 5 | 5 | 5 | 5 |
| Diethylamino hydroxybenzoyl hexyl benzoate | 1 | 1 | 1 | 1 | 1 | 1 | 1 | 1 |
| bis-Ethylhexyloxyphenol methoxyphenyl triazine | 1 | 1 | 1 | 1 | 1 | 1 | 1 | 1 |
| Homosalate | 3 | 3 | 3 | 3 | 3 | 3 | 3 | 3 |
| Octyl salicylate | 5 | 5 | 5 | 5 | 5 | 5 | 5 | 5 |
| Ethylhexyl triazone | 0.5 | 0.5 | 0.5 | 0.5 | 0.5 | 0.5 | 0.5 | 0.5 |
| Total | 100 | 100 | 100 | 100 | 100 | 100 | 100 | 100 |
| 4-tert-Butyl-4'-methoxybenzoyl methane/total amount of ultraviolet protectant | 2.0% | 3.9% | 7.8% | 11.8% | 2.0% | 3.9% | 7.8% | 11.8% |
| Thermal reaction rate | 113% | 111% | 107% | 104% | 110% | 106% | 105% | 103% |

As shown in Table 8, when t-butyl methoxy dibenzoyl methane (4-tert-butyl-4'-methoxy dibenzoyl methane) was blended as the (A) ultraviolet protectant, a high thermal reaction rate was obtained by setting the blended amount thereof to be 10% by mass or less relative to the total amount of the (A) ultraviolet protectant.

Hereinafter, examples of formulations of the cosmetic of the present invention will be indicated. Needless to say, the present invention is not limited in any way by these formulation examples, and is as defined by the claims. The blended amounts are all indicated in percentage by mass relative to the total amount of the cosmetic.

Formulation example 1: Makeup base (liquid)

| (Component name) | Blended amount (% by mass) |
|---|---|
| Isododecane | balance |
| Diisopropyl sebacate | 30 |
| Ethanol | 10 |
| PEG/PPG-9/2 dimethyl ether | 20 |
| Ethylhexyl methoxycinnamate | 10 |
| Octyl salicylate | 5 |
| bis-Ethylhexyloxyphenol methoxyphenyl triazine | 2 |
| Octocrylene | 5 |
| Diethylamino hydroxybenzoyl hexyl benzoate | 2 |
| Isostearic acid | 2 |
| Polymethyl methacrylate | 6 |
| Hydrophobically treated silica | 0.5 |
| Hydrophobic fine-particle titanium oxide | 1 |
| Hydrophobic fine-particle zinc oxide | 1 |
| Hydrophobically treated iron oxide | 0.7 |
| Hydrophobically treated barium sulfate-coated titanated mica | 0.01 |
| Hydrophobically treated titanated mica | 0.01 |

Formulation example 2: Aerosol spray-type sunscreen

| (Component name) | Blended amount (% by mass) |
|---|---|
| Isododecane | balance |
| Diisopropyl sebacate | 20 |

-continued

| Formulation example 2: Aerosol spray-type sunscreen | |
|---|---|
| (Component name) | Blended amount (% by mass) |
| Glyceryl tri-2-ethylhexanoate | 5 |
| Isopropyl myristate | 6 |
| Ethanol | 7 |
| PEG/PPG-9/2 dimethyl ether | 20 |
| Ethylhexyl methoxycinnamate | 10 |
| Octyl salicylate | 5 |
| bis-Ethylhexyloxyphenol methoxyphenyl triazine | 2 |
| Octocrylene | 5 |
| Diethylamino hydroxybenzoyl hexyl benzoate | 2 |
| Isostearic acid | 2 |
| Polymethyl methacrylate | 6 |
| Hydrophobically treated silica | 0.5 |

The above-mentioned components were mixed to form a stock solution, and a spray can was filled with the stock solution and LPG at a ratio of 50:50 to obtain an aerosol spray-type sunscreen.

| Formulation example 3: Lipstick | |
|---|---|
| (Component name) | Blended amount (% by mass) |
| Diisopropyl sebacate | balance |
| Hydrogenated polydecene | 20 |
| Diphenylsiloxyphenyl trimethicone | 2 |
| PEG/PPG-9/2 dimethyl ether | 15 |
| Ethylhexyl methoxycinnamate | 10 |
| 4-tert-butyl-4'-methoxybenzoyl methane | 3 |
| Homosalate | 10 |
| bis-Ethylhexyloxyphenol methoxyphenyl triazine | 2 |
| Octocrylene | 5 |
| Diethylamino hydroxybenzoyl hexyl benzoate | 3 |
| Hydroxystearic acid | 6 |
| Polyamide-8 | 2 |
| Dibutyllauroyl glutamide | 2 |
| Pigment | 0.03 |

The invention claimed is:

1. An oil-based cosmetic containing
   (A) an ultraviolet protectant; and
   (B) polyoxyalkylene/polyoxyethylene copolymer dialkyl ethers represented by the following formula (I):

$$R_1O-[(AO)_m(EO)_n]-R_2 \quad (I)$$

wherein $R_1$ and $R_2$, each independently, denote a hydrogen atom or a hydrocarbon group having one to four carbon atoms, AO denotes an oxyalkylene group having three or four carbon atoms, EO denotes an oxyethylene group, $m+n \leq 20$; and
   the oil-based cosmetic has a water content of 5% by mass or less.

2. The oil-based cosmetic as in claim 1, wherein the (A) ultraviolet protectant contains 4-tert-butyl-4'-methoxy dibenzoyl methane, and a blended amount thereof is 10% by mass or less relative to a total amount of the (A) ultraviolet protectant.

3. The oil-based cosmetic as in claim 1, wherein the oil-based cosmetic further comprises polyhydric alcohols selected from the group consisting of polyalkylene glycol, butylene glycol, dipropylene glycol, diglycerin, propanediol, erythritol, xylitol, methylglyceth-10 and sorbitol; and
   the polyalkylene glycol is represented by the following formula (II):

$$HO(RO)_pH \quad (II)$$

wherein RO denotes an oxyalkylene group having two to four carbon atoms and p is 3 to 500.

4. The oil-based cosmetic as in claim 3, wherein the polyhydric alcohols are polyethylene glycols having an average molecular weight of 150 to 23000.

5. The oil-based cosmetic as in claim 1, wherein a blended amount of component (B) is 2.5% by mass or more relative to the total amount of the oil-based cosmetic.

6. The oil-based cosmetic as in claim 1, further containing a solidifier.

7. The oil-based cosmetic as in claim 1, wherein the oil-based cosmetic is an unseparated single phase.

8. The oil-based cosmetic as in claim 1, wherein the oil-based cosmetic is transparent.

9. The oil-based cosmetic as in claim 1, wherein the oil-based cosmetic is in gel form and has a viscosity, at 25° C., of 300 mPa·s or higher.

10. The oil-based cosmetic as in claim 1, wherein the oil-based cosmetic is in solid form and has a hardness, at 25° C., of 5 N or higher.

* * * * *